United States Patent [19]

Abe et al.

[11] Patent Number: 5,008,479
[45] Date of Patent: Apr. 16, 1991

[54] PROCESS FOR PRODUCTION OF 2,6-DIMETHYLNAPHTHALENE

[75] Inventors: Takafumi Abe; Seiji Uchiyama; Takahiro Ojima; Koichi Kida, all of Niigata, Japan

[73] Assignee: Mitsubishi Gas Chemical Company, Inc., Tokyo, Japan

[21] Appl. No.: 375,860

[22] Filed: Jul. 5, 1989

[30] Foreign Application Priority Data

Sep. 27, 1988 [JP] Japan ................... 63-239762

[51] Int. Cl.$^5$ ............ C07C 1/00; C07C 11/253; C07C 1/20
[52] U.S. Cl. ................... 585/320; 585/321; 585/322; 585/409; 585/469; 585/410; 585/411; 549/242; 568/311; 568/814
[58] Field of Search ........... 585/320, 321, 322, 409, 585/469, 410, 411; 568/311, 814; 549/242

[56] References Cited

U.S. PATENT DOCUMENTS

| 2,575,403 | 11/1951 | Young et al. ................. 585/814 |
| 2,848,509 | 8/1958 | Toland et al. ................. 585/321 |
| 3,391,348 | 1/1976 | Taniguichi et al. . |
| 3,806,548 | 4/1974 | Harpold et al. ................. 568/311 |
| 3,944,627 | 3/1976 | Schram et al. . |
| 4,487,972 | 11/1984 | Haag et al. ................. 568/311 |

FOREIGN PATENT DOCUMENTS

| 2211426 | 7/1974 | France . |
| 2230606 | 12/1974 | France . |
| 50-012429 | 5/1975 | Japan . |
| 1204147 | 9/1986 | Japan ................. 568/814 |

Primary Examiner—H. M. S. Sneed
Assistant Examiner—James Saba
Attorney, Agent, or Firm—Frishauf, Holtz, Goodman & Woodward

[57] ABSTRACT

A process for production of 2,6-dimethylnaphthalene is disclosed, comprising the steps: (1) an acylation step where p-tolyl sec-butyl ketone is produced from toluene, n-butene and carbon monoxide: (2) a hydrogenation step where the carbonyl group of the p-tolyl sec-butyl ketone is hydrogenated: and (3) a dehydrogenation and cyclization step where the hydrogenated product obtained above is subjected to dehydrogenation and cyclization to produce the desired 2,6-dimethylnaphthalene. The process enables efficiently producing a high quality or high purity 2,6-dimethylnaphthalene.

36 Claims, No Drawings

PROCESS FOR PRODUCTION OF 2,6-DIMETHYLNAPHTHALENE

BACKGROUND OF THE INVENTION

1. Field of the Invention

The present invention relates to a process for production of 2,6-dimethylnaphthalene and more particularly to a process for producing 2,6-dimethylnaphthalene on a commercial scale from toluene, n-butene and carbon monoxide as starting materials to produce p-tolyl sec-butyl ketone.

2. Description of the Related Arts 2,6-Dimethylnaphthalene is generally used as a starting material for producing industrially useful 2,6-naphthalene dicarboxylic acid through oxidation. This 2,6-naphthalene dicarboxylic acid is used, for example, for producing polyethylene terephthalate fibers or films having excellent tensile strength and thermal resistance.

2,6-Dimethylnaphthalene which is such a useful chemical material, has heretofore been obtained by isolating it from a tar fraction. However, in this method of isolating from a tar fraction, only a small amount of 2,6-dimethylnaphthalene can be obtained and moreover its separation or purification is difficult. Thus this method using a tar fraction as a starting material cannot be said to be a method suitable for industrial production of 2,6-dimethylnaphthalene in large quantities and at low production costs.

In recent years, various methods of synthesizing 2,6-dimethylnaphthalene from various starting materials have been proposed. In fact, however, no industrial methods of production whereby 2,6-dimethylnaphthalene can be synthesized effectively and selectively from an inexpensive starting material have been developed.

For example, Japanese Patent Publication Nos. 17983/1975, 17984/1975 and 17985/1975 disclose methods in which 5-(o-tolyl)pentene-2 is used as a starting material and it is subjected to dehydrogenation and cyclization to produce 2,6-dimethylnaphthalene and other dimethylnaphthalenes. In general, the 5-(o-tolyl)-pentene-2 to be used as a starting material in the above method is synthesized from o-xylene and 1,3-butadiene. In this reaction, however, alkylation of the methyl group in the o-xylene is unpractical and, therefore, the production of 5-(o-tolyl)pentene-2 itself is not easy. Also during the dehydrogenation and cyclization steps of 5-(o-tolyl)pentene-2, a number of dimethylnaphthalene isomers other than 2,6-dimethylnaphthalene are formed and, therefore, an isomerization step and a complicated separation and purification step are required.

Japanese Patent Publication Nos. 1701/1976 and 5292/1978 disclose methods in which an alkylated product from toluene or p-xylene is used as a starting material and it is subjected to dehydrogenation and cyclization to produce various types of dimethylnaphthalenes, as well as 2,6-dimethylnaphthalene. In particular, Japanese Patent Publication No. 5292/1978 discloses a method in which 3-methyl-4-(p-tolyl)-butane obtained by the side chain alkylation of p-xylene with butene-1 is used as a starting material and it is subjected to dehydrogenation and cyclization to produce 2,6-dimethylnaphthalene. However, since a large amount of an alkali metal such as sodium or potassium is generally used in the side chain alkylation, the starting material itself becomes expensive. Moreover, in the dehydrogenation and cyclization reaction of the starting material, a number of dimethylnaphthalene isomers other than 2,6-dimethylnaphthalene are also produced. Thus the above method cannot be said to be an industrially satisfactory method.

SUMMARY OF THE INVENTION

An object of the present invention is to provide a process for industrial production of 2,6-dimethylnaphthalene using inexpensive compounds as starting materials.

Another object of the present invention is to provide a process for efficiently producing high purity 2,6-dimethylnaphthalene not containing any isomers.

The present invention relates to a process for producing 2.6-dimethylnaphthalene which comprises the following three steps:

(1) an acylation step to synthesize p-tolyl sec-butyl ketone from toluene, n-butene and carbon monoxide;

(2) a hydrogenation step to hydrogenate the carbonyl group of the p-tolyl sec-butyl ketone; and (3) a dehydrogenation and cyclization step to dehydrogenate and cyclize the hydrogenated product obtained in (2) above, thereby producing the desired 2,6dimethylnaphthalene.

DESCRIPTION OF THE PREFERRED EMBODIMENTS

It will hereinafter be explained in detail how the present invention has been accomplished.

When toluene, n-butene and carbon monoxide as starting materials were subjected to acylation in the presence of a Lewis acid catalyst, e.g., boron trifluoride or aluminum chloride, selective substitution of the toluene with an acyl group at the p-position thereof occurred, whereby p-tolyl sec-butyl ketone was formed. In this substitution reaction, almost no isomer was formed, the yield of p-tolyl sec-butyl ketone was high, and the separation of the catalyst was easy.

The present inventors made extensive investigations to synthesize 2,6-dimethylnaphthalene from p-tolyl sec-butyl ketone as obtained above. An attempt to synthesize 2,6-dimethylnaphthalene directly from p-tolyl sec-butyl ketone was made but with no success.

On the other hand, it has been found that if the carbonyl group of p-tolyl sec-butyl ketone is hydrogenated to produce p-tolyl-sec-butylcarbinol, 2-methyl-1-(p-tolyl)butane and 2-methyl-1-(p-tolyl)-butene and then each of the compounds or a mixture thereof is subjected to a dehydrogenation and cyclization reaction, 2,6-dimethylnaphthalene can be obtained in a high yield.

In the hydrogenation reaction of p-tolyl sec-butyl ketone, it is preferred that p-tolyl sec-butyl ketone be converted into 2-methyl-1-(p-tolyl)-butene because it requires a particularly small amount of hydrogen for production thereof, among the above three hydrogenated products. Moreover when 2-methyl-1-(p-tolyl)-butene was subjected to dehydrogenation and cyclization reactions, 2,6-dimethylnaphthalene could be obtained in the highest yield.

Thus, in order to produce mainly 2-methyl-1-(p-tolyl)butene, it is preferred that p-tolyl-sec-butylcarbinol is selectively formed in the hydrogenation reaction of p-tolyl sec-butyl ketone, and then is subjected to the dehydration reaction.

2,6-Dimethylnaphthalene produced by the process of the present invention contains almost no isomers. Thus neither an isomerization step nor a separation step is needed, and high purity 2,6-dimethylnaphthalene can be easily obtained by applying the usual operations such as distillation and recrystallization.

The scheme of reaction which occurs in the process of the present invention is shown below for easier understanding thereof.

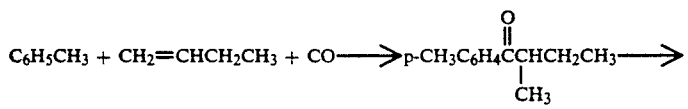

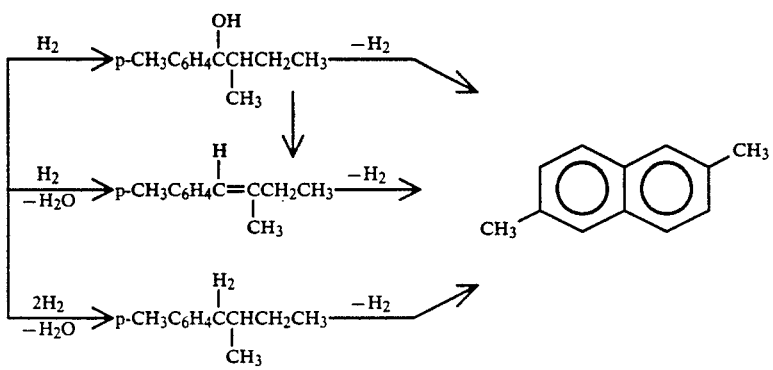

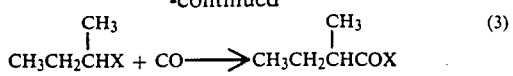

Each step of the process of the present invention will hereinafter be explained in detail.

Acylation Step

Predetermined amounts of an anhydrous hydrogen halide (HF, HCl or HBr) and a Lewis acid catalyst ($BF_3$ or $AlCl_3$) are placed in an anticorrosive (SUS-316 or Hastelloy C) autoclave, and then carbon monoxide is introduced under a pressure of 1 to 150 kg/$cm^2$, preferably 10 to 80 kg/$cm^2$. The temperature is chosen within the range of 0 to 100° C., and preferably 10 to 60° C. Then n-butene or 2-halobutane formed according to the following reaction formula (1):

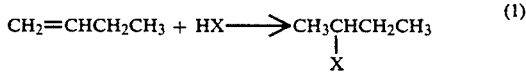

(wherein X is F, Cl or Br) is continuously introduced.

As the n-butene to be used in the reaction, butene-1, butene-2 (including both cis-butene-2 and trans-butene-2), or a mixture thereof can be used. In addition, butene-1, butene-2 or a mixture thereof, containing saturated hydrocarbons such as n-butane can be used. For example, so-called spent "spent BB (SS-BB)" obtained after extraction of butadiene, isobutylene, etc. from a BB fraction can be used.

In this acylation reaction, it is necessary that sufficient gas-liquid contact is accomplished by stirring in the reactor.

In connection with n-butene and carbon monoxide to be used in the reaction, high purity is preferable, and it is desirable that water, carbon dioxide gas, etc. be removed to the utmost.

The present reaction proceeds according to the route represented by the following formula (2) or (3):

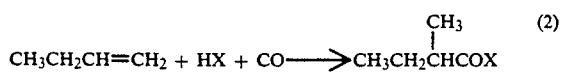

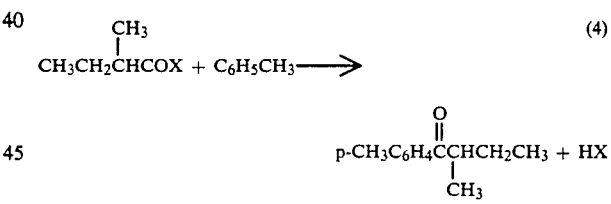

(wherein X is the same as defined above), and 2-methyl butanoyl halide results.

After removal of carbon monoxide from the reaction system, a Lewis acid, e.g., $BF_3$ or $AlCl_3$, is added to the reaction product solution to prepare a reaction mixture.

Toluene is introduced with stirring into the above mixture, and is reacted therewith.

The reaction proceeds as shown in the following formula (4):

$$\begin{array}{c} CH_3 \\ | \\ CH_3CH_2CHCOX + C_6H_5CH_3 \longrightarrow \end{array} \quad (4)$$

$$\begin{array}{c} O \\ \| \\ p\text{-}CH_3C_6H_4CCHCH_2CH_3 + HX \\ | \\ CH_3 \end{array}$$

(wherein X is the same as defined above).

In the reaction, the temperature is −10° to 60° C. and preferably 0° to 40° C., and the reaction is completed in a residence time of 15 to 180 minutes.

The acylation reaction in the process of the present invention comprises a series of reaction steps as described above. The formulae (1), (3) and (4) or the formulae (2) and (4) can be summarized as shown below.

The acylation reaction can be carried out batchwise or continuously. Separation of the catalyst from the reaction product is usually carried out by a phase separation method or a thermal decomposition method.

Hydrogenation Step

Hydrogenation of p-tolyl sec-butyl ketone obtained during the acylation step can be carried out by various methods. In practice, p-tolyl sec-butyl ketone is contacted with hydrogen in a liquid phase in the presence of a solid catalyst.

As the catalyst; a Raney type catalyst such as Raney nickel or Raney cobalt, a copper chromium-base catalyst, a metal oxide catalyst such as a nickel oxide catalyst or a cobalt oxide catalyst, or a noble metal catalyst comprising alumina or active carbon with a noble metal such as platinum or palladium deposited thereon, is effectively used.

In the practice of the hydrogenation reaction, the type of the catalyst and the reaction conditions are determined depending on the desired hydrogenated product. In general, the hydrogen pressure is 1 to 100 kg/cm$^2$ and preferably 5 to 50 kg/cm$^2$, and the reaction temperature is 30° to 300° C. and preferably 60° to 200° C.

The hydrogenation reaction can be carried out batchwise or continuously. In practice, a trickle type reaction system using a fixed bed catalyst is usually employed.

Dehydration Step

2-Methyl-(p-tolyl)-butene can be produced even by hydrogenating p-tolyl sec-butyl ketone, but its yield is not always satisfactory. Rather it can be obtained with high yield by dehydration of p-tolyl-sec-butylcarbinol.

This dehydration reaction is carried out by a gas phase reaction using a catalyst such as active alumina or silica alumina. The reaction temperature is 200° to 400° C. and preferably 250° to 350° C., and 2-methyl-(p-tolyl)-butene can be obtained in a high yield.

In the process of the present invention, the dehydration step can be omitted. 2-Methyl-(p-tolyl)-butene obtained by dehydration of p-tolyl-sec-butylcarbinol is effective as a starting material for use in the dehydrogenation and cyclization reaction as described hereinafter.

Dehydrogenation and Cyclization Step 2,6-Dimethylnaphthalene can be produced from any of p-tolyl-sec-butylcarbinol, 2-methyl-(p-tolyl)-butane and 2-methyl-(p-tolyl)-butene by a dehydrogenation and cyclization reaction. The dehydrogenation and cyclization reaction is carried out by contacting the starting material with a solid catalyst in a gas phase at an elevated temperature.

As the catalyst, a metal oxide catalyst such as an alumina chromia catalyst or an iron oxide catalyst, or a catalyst comprising alumina or active carbon with noble metal such as platinum or palladium deposited thereon is suitably used.

The reaction temperature is 350° to 700° C. and preferably 450° to 600° C.

The reaction pressure is not critical and the reaction can be carried out under reduced pressure, atmospheric pressure, or high pressure. The reaction is usually carried out in the range of atmospheric pressure to 2 kg/cm$^2$.

As the reaction type; a fixed bed adiabatic type, a fixed bed shell and tube type, or a fluid bed type is employed.

The reaction mixture obtained during the cyclization and dehydrogenation step contains, as well as the objective 2,6-dimethylnaphthalene not containing isomers, unreacted starting materials and by-products such as β-methyl naphthalene and p-xylene.

A high purity 2,6-dimethylnaphthalene product can be easily obtained by distillation or recrystallization of the above reaction mixture. Unreacted starting materials recovered are re-used in the reaction.

In accordance with the process of the present invention, high purity 2,6-dimethylnaphthalene not containing isomers can be produced from toluene, n-butene and carbon monoxide as starting materials through the p-tolyl sec-butyl ketone formed. Thus the process of the present invention is of high industrial significance as a method for inexpensively producing high purity 2,6-dimethylnaphthalene.

The present invention is described in greater detail with reference to the following examples.

EXAMPLE (1) Acylation Step

Sixty grams of HF and 2.1 g of BF$_3$ were placed in a 100-ml autoclave (Hastelloy C), and CO was introduced until the pressure reached 20 kg/cm$^2$G. While vigorous stirring, 16.8 g of 1-butene was continuously introduced thereto over 30 minutes.

The reaction temperature was maintained at 30° C., and the pressure in the system was maintained at 20 kg/cm$^2$G by compensating for the absorbed CO. After completion of CO absorption, the reaction mixture was cooled and the remaining CO was purged.

Then, 20.1 g of fresh BF$_3$ was added again to adjust the catalyst ratio. The reaction temperature was maintained at 5° C., and 27.6 g of toluene was introduced while stirring over 15 minutes. Then the reaction temperature was raised to 25° C. and stirring was continued for 30 minutes to complete the reaction.

The yield of p-tolyl sec-butyl ketone was 93% based on the weight of toluene.

(2) Hydrogenation Step

A SUS 316 reactor (diameter: 15 mm; length: 300mm) was packed with 18 g of a copper chromite catalyst (N-201 catalyst produced by Nikki Chemical Co., Ltd.). According to a trickel type reaction system, a starting material of p-tolyl-sec-butyl ketone was introduced into a catalyst layer through a preheating layer at a rate of 18 g/hour under a hydrogen pressure of 6 kg/cm$^2$G at a catalyst layer temperature of 150° C.

An analysis of the reaction mixture showed that the conversion of p-tolyl sec-butyl ketone was 90% and the selectivity to p-tolyl-sec-butylcarbinol was 98%.

(3) Dehydration Step

The p-tolyl-sec-butylcarbinol as obtained above was used as a starting material and reacted as follows.

A heat-resistant glass (Pyrex glass) reaction tube (diameter: 15 mm; length: 300 mm) was charged with 15 g of active alumina (Neobead GB produced by Mizusawa Kagaku Co., Ltd.). The catalyst layer temperature was maintained at 300° C., and the gaseous p-tolyl-sec-butylcarbinol as starting material was introduced in admixture with a small amount of N$_2$ gas into a catalyst layer through a preheating layer at a rate of 15 g/hour.

An analysis of the reaction mixture showed that the conversion of p-tolyl-sec-butylcarbinol was 100%, and the selectivity to 2-methyl-(p-tolyl)-butene was 99%.

(4) Dehydrogenation and Cyclization Step

A quartz glass reaction tube (diameter: 12 mm; length: 300 mm) was charged with 10 g of a 10% Cr$_2$O$_3$-5% K$_2$O-Al$_2$O$_3$ catalyst, and the catalyst layer was maintained at 500° C.

A 10% solution of 2-methyl-(p-tolyl)-1-butene dissolved in toluene was vaporized by passing through a preheating layer at a rate of 10 g/hour and introduced into the catalyst layer in admixture with 30 ml/minute of $N_2$ gas.

An analysis of the reaction mixture showed that the conversion of 2-methyl(p-tolyl)-butene was 93% and the selectivity to 2,6-dimethylnaphthalene was 71%.

What is claimed is:

1. A process for producing 2,6-dimethylnaphthalene which comprises the following three steps: (1) reacting toluene, n-butene and carbon monoxide to produce p-tolyl sec-butyl ketone; (2) hydrogenating the carbonyl group of said p-tolyl sec-butyl ketone; and (3) dehydrogenating and cyclizing said hydrogenated p-tolyl sec-butyl ketone to produce said 2,6-dimethylnaphthalene.

2. A process for producing 2,6-dimethylnaphthalene which comprises the following four steps: (1) reacting toluene, n-butene and carbon monoxide to produce p-tolyl sec-butyl ketone; (2) hydrogenating the carbonyl group of said p-tolyl sec-butyl ketone to produce p-tolyl-sec-butylcarbinol; (3) dehydrating said p-tolyl-sec-butylcarbinol to produce 2-methyl-(p-tolyl)-butene; and (4) dehydrogneating and cyclizing said 2-methyl-(p-tolyl)-butene to produce 2,6-dimethylnaphthalene.

3. The process as claimed in claim 1 wherein the hydrogneated product obtained by step (2) is p-tolyl-sec-butylcarbinol.

4. The process as claimed in claim 1 wherein the hydrogenated product obtained by the hydrogenation step (2) is 2-methyl-(p-tolyl)-butane.

5. The process as claimed in claim 1 wherein the hydrogenated product obtained by the hydrogenation step (2) is 2-methyl-(p-tolyl)-butene.

6. The process as claimed in claim 1 wherein the hydrogenated product obtained by the hydrogenation step (2) is a mixture of p-tolyl-sec-butylcarbinol, 2-methyl-(p-tolyl)-butane and 2-methyl-(p-tolyl)-butene.

7. The process as claimed in claim 1 wherein the step (1) is carried out in the presence of a Lewis acid.

8. The process as claimed in claim 1 wherein the step (2) is carried out in the presence of a solid catalyst.

9. The process as claimed in claim 8 wherein the solid catalyst is a Raney catalyst, a copper chromium catalyst, a metal oxide catalyst or a noble metal catalyst.

10. The process as claimed in claim 1 wherein the dehydrogenating and cyclizing is carried out in the presence of a solid catalyst.

11. The process as claimed in claim 10 wherein the solid catalyst is an alumina chromia catalyst, a metal oxide catalyst or a noble metal catalyst.

12. The process as claimed in claim 2 wherein the dehydration step (3) is carried out in the presence of a catalyst.

13. The process as claimed in claim 12 wherein the catalyst is active alumina or silica alumina.

14. The process as claimed in claim 1, wherein the step (1) is carried out by (a) introducing the carbon monoxide at a pressure of 1 to 150 kg/cm$^2$ and the n-butene in the presence of an anhydrous hydrogen halide selected from the group consisting of HF, HCl and HBr and a Lewis acid catalyst selected from the group consisting of $BF_3$ and $AlCl_3$ at a temperature of 0 to 100° C., (b) removing remaining carbon monoxide from the resultant reaction system, adding a Lewis acid selected from the group consisting of $BF_3$ and $AlC_3$ and introducing toluene at a temperature of −10 to 60° for a residence time of 15 to 180 minutes.

15. The process as claimed in claim 14, wherein for (a), the temperature is 10 to 60 ° C. and the carbon monoxide is introduced under a pressure of 10 to 80 kg/cm$^2$ and for (b), the temperature is 0 to 40° C.

16. The process as claimed in claim 1, wherein the hydrogenating is conducted at 30 to 300° C. using hydrogen at a pressure of 1 to 100 kg/cm$^2$.

17. The process as claimed in claim 1, wherein the hydrogenating step is conducted at 60 to 200° C. using hydrogen at a pressure of 5 to 50 kg/cm$^2$.

18. The process as claimed in claim 17, wherein the hydrogenating is conducted in the presence of a catalyst selected from the group consisting of Raney nickel, Raney cobalt, a nickel oxide catalyst, a cobalt oxide catalyst, a copper chromium-base catalyst, a platinum catalyst and a palladium catalyst.

19. The process as claimed in claim 1, wherein the dehydrogenating and cyclizing is conducted at a temperature of 350 to 700° C. and at or pressure of atmospheric pressure to 2 kg/cm$^2$.

20. The process as claimed in claim 1 wherein the dehydrogenating and cyclizing is conducted at a temperature of 450° to 600° C.

21. The process as claimed in claim 2 wherein the step (1) is carried out by (a) introducing the carbon monoxide at a pressure of 1 to 150 kg/cm$^2$ and the n-butene in the presence of an anhydrous hydrogen halide selected from group consisting of HF, HCl and HBr and a Lewis acid catalyst selected from the group consisting of $BF_3$ and $AlCl_3$ at a temperature of 0° to 100° C., (b) removing remaining carbon monoxide from the resultant reaction system, adding a Lewis acid selected from the group consisting of $BF_3$ and $AlCl_3$ and introducing toluene at a temperature of −10° to 60° C. for a residence time of 15 to 180 minutes.

22. The process as claimed in claim 21, wherein for (a), the temperature is 10° to 60° C. and the carbon monoxide is introduced under a pressure of 10 to 80 kg/cm$^2$ and for (b), the temperature is 0° to 40° C.

23. The process as claimed in claim 2, wherein the hydrogenating is conducted 30° to 300° C. using hydrogen at a pressure of 1 to 100 kg/cm$^2$.

24. The process as claimed in claim 2, wherein the hydrogenating is conducted 60° to 200° C. using hydrogen at a pressure of 5 to 50 kg/cm$^2$.

25. The process as claimed in claim 24, wherein the hydrogenating is conducted in the presence of a catalyst selected from the group consisting of Raney nickel, Raney cobalt, a nickel oxide catalyst, a cobalt oxide catalyst, a copper chromium-base catalyst, a platinum catalyst and a palladium catalyst.

26. The process as claimed in claim 2, wherein the dehydrogenating and cyclizing is conducted at a temperature of 350° to 700° C. and at a pressure of atmospheric pressure to 2 kg/cm$^2$.

27. The process as claimed in claim 2, wherein the dehydrogenating and cyclizing is conducted at a temperature of 450° to 600° C.

28. The process as claimed in claim 2, wherein the dehydrating is conducted at a temperature of 200° to 400° C.

29. The process as claimed in claim 2, wherein the dehydrating is conducted at a temperature of 250° to 350° C.

30. The process as claimed is claim 2, wherein the dehydrogenating and cyclizing is carried out in the presence of a solid catalyst selected from the group consisting of an alumina chromia catalyst, a metal oxide catalyst and a noble metal catalyst.

31. The process as claimed in claim 1, wherein the hydrogenation product obtained by the step (2) is selected from the group consisting of p-tolyl-sec-butylcarbinol, 2-methyl-2-tolyl)-butane, 2-methyl-(p-tolyl)-butene and a mixture of p-tolyl-sec-butylcarbinol, 2-methyl-(p-tolyl)-butane and 2-methyl-(p-tolyl)-butene, wherein the step(1) is carried out in the presence of a solid catalyst selected from the group consisting of a Raney catalyst, a copper chromium catalyst, a metal oxide catalyst and a noble metal catalyst and wherein the dehydrogenating and cyclizing is carried out in the presence of a solid catalyst selected from the group consisting of an alumina chroma catalyst, a metal oxide catalyst and a noble metal catalyst.

32. The process of claim 2, wherein the step(1) is carried out in the presence of an anhydrous hydrogen halide selected from the group consisting of HF, HCl and HBr and a Lewis acid selected from the group consisting of $BF_3$ and $AlCl_3$, the hydrogneating step(2) is carried out in the presence of a solid catalyst selected from the group consisting of a Raney catalyst, a copper chromium catalyst, a metal oxide catalyst and a noble metal catalyst, the dehydration step(3) is carried out in the presence of a catalyst selected from the group consisting of an active alumina and a silica alumina and the dehydrogenating and cyclization step(4) is carried out in the presence of a solid catalyst selected from the group consisting of an alumina chromia catalyst, a metal oxide catalyst and a noble metal catalyst.

33. The process of claim 1, wherein the step(1) is carried out in the presence of an anhydrous hydrogen halide selected from the group consisting of HF, HCl and HBr and a Lewis acid selected from the group consisting of $BF_3$ and $AlCl_3$, the hydrogenating step (2) is carried out in the presence of a solid catalyst selected from the group consisting of a Raney catalyst, a copper chromium catalyst and a metal oxide catalyst at a temperature of 60° to 200° C. using hydrogen at a pressure of 5 to 50 kgs/cm$^2$ and the dehydrogenating and cyclizing is carried out in the presence of a solid catalyst selected from the group consisting of an alumina chromia catalyst, a metal oxide catalyst and a noble metal catalyst at a temperature of 450° C. to 600° C. and at a pressure of 2 kg/cm$^2$.

34. The process of claim 2, wherein the step(1) is carried out in the presence of a Lewis acid selected from the group consisting of $BF_3$ and $AlCl_3$, the hydrogenating step (2) is carried out in the presence of a solid catalyst selected from the group consisting of a Raney catalyst, a copper chromium catalyst, a metal oxide catalyst and a noble metal catalyst at a temperature of 60° to 200° C. using hydrogen at a pressure of 5 to 50 kg/cm$^2$, the dehydration step (3) is carried out in the presence of a catalyst selected from the group consisting of an active alumina and a silica alumina at a temperature of 250° C. to 350° C. and the dehydrogenating and cyclization step (4) is carried out in the presence of a solid catalyst selected from the group consisting of an alumina chromia catalyst, a metal oxide catalyst and a noble metal catalyst at a temperature of 450° to 600° C. and at a pressure of 2 kg/cm$^2$.

35. The process of claim 33, wherein in step(1) the hydrogen halide is HF and the Lewis acid is $BF_3$, wherein in the hydrogenating step (2), the catalyst is a copper chromium catalyst and wherein in the dehydrogenating and cyclizing step (3) the catalyst is an alumina chromia catalyst comprising $Cr_2O_3$—$K_2O$—$Al_2O_3$.

36. The process of claim 34, wherein in step(1) the hydrogen halide is HF and the Lewis acid is $BF_3$, wherein in the hydrogenating step(2), the catalyst is a copper chromium catalyst, wherein in the dehydrating step(3), the catalyst is an active alumina and wherein in the dehydrogenating and cyclizing step (4), the catalyst is an alumina chromia catalyst comprising $C_2O_3$—$K_2O$—$Al_2O_3$.

* * * * *